US010668278B2

(12) United States Patent
Heller et al.

(10) Patent No.: US 10,668,278 B2
(45) Date of Patent: Jun. 2, 2020

(54) EXPANDABLE CATHETER DEVICES ELECTRODE ARRAY (71) Applicant: Old Dominion University Research Foundation, Norfolk, VA (US)

(72) Inventors: Richard Heller, Norfolk, VA (US); Chen Yeong-Jer, Norfolk, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 500 days.

(21) Appl. No.: 15/311,130

(22) PCT Filed: Mar. 24, 2015

(86) PCT No.: PCT/US2015/022145
§ 371 (c)(1),
(2) Date: Nov. 14, 2016

(87) PCT Pub. No.: WO2015/148445
PCT Pub. Date: Oct. 1, 2015

(65) Prior Publication Data
US 2017/0072193 A1    Mar. 16, 2017

Related U.S. Application Data (60) Provisional application No. 61/969,386, filed on Mar. 24, 2014.

(51) Int. Cl.
*A61B 1/00* (2006.01)
*A61N 1/32* (2006.01)
(Continued)

(52) U.S. Cl.
CPC .............. *A61N 1/327* (2013.01); *A61B 1/005* (2013.01); *A61B 1/018* (2013.01); *A61B 1/04* (2013.01);
(Continued)

(58) Field of Classification Search
CPC ............ A61B 1/00174; A61B 1/00179; A61B 1/00183; A61B 1/00066
(Continued)

(56) References Cited

U.S. PATENT DOCUMENTS 4,737,142 A    4/1988  Heckele
5,267,994 A *  12/1993 Gentelia ............ A61B 18/1482
                                                      604/35
(Continued)

FOREIGN PATENT DOCUMENTS

CN          101563132       10/2009

OTHER PUBLICATIONS

AU Examination Report No. 1 in Australian Appln. No. 2015236341, dated Mar. 13, 2019, 5 pages.
(Continued)

*Primary Examiner* — Matthew J Kasztejna
(74) *Attorney, Agent, or Firm* — Fish & Richardson P.C.

(57) ABSTRACT

Catheter devices can include an elongate housing extending along a major axis, the elongate housing comprising a first end an opening. The catheter devices can also include an electrode assembly disposed in the elongate housing and including deformable electrodes with respective electrode distal ends, where the electrode distal ends each consist of respective member portions and respective tip portions. The electrode assembly is slidably movable within the housing along the major axis to allow the electrode distal end portions to transition between a first retracted position and a second extended position. The catheter device is configured such that an average distance between the tip portions in the second position is configured to be greater than an average distance between the tip portions in the first position the tip portions are positioned substantially in a same plane when the electrode assembly is in the second position.

26 Claims, 8 Drawing Sheets (51) Int. Cl.
*A61B 18/14* (2006.01)
*A61N 1/36* (2006.01)
*A61N 1/05* (2006.01)
*A61B 1/005* (2006.01)
*A61B 1/018* (2006.01)
*A61B 1/04* (2006.01)
*A61B 1/06* (2006.01)
*A61M 5/158* (2006.01)
*A61B 18/00* (2006.01)
*A61B 18/12* (2006.01)

(52) U.S. Cl.
CPC ............ *A61B 1/06* (2013.01); *A61B 18/1492* (2013.01); *A61M 5/158* (2013.01); *A61N 1/0502* (2013.01); *A61N 1/36002* (2017.08); *A61B 18/1477* (2013.01); *A61B 2018/0016* (2013.01); *A61B 2018/00214* (2013.01); *A61B 2018/00982* (2013.01); *A61B 2018/124* (2013.01); *A61B 2018/143* (2013.01); *A61B 2018/1465* (2013.01); *A61B 2018/1475* (2013.01)

(58) Field of Classification Search
USPC ........................................................ 600/151
See application file for complete search history.

(56) References Cited

U.S. PATENT DOCUMENTS

| | | | | |
|---|---|---|---|---|
| 5,300,069 | A * | 4/1994 | Hunsberger | A61B 18/1482 606/29 |
| 5,322,503 | A * | 6/1994 | Desai | A61B 17/00234 604/21 |
| 5,551,426 | A * | 9/1996 | Hummel | A61B 5/0422 600/374 |
| 5,607,435 | A * | 3/1997 | Sachdeva | A61B 1/0058 359/819 |
| 5,674,267 | A | 10/1997 | Mir et al. | |
| 5,993,447 | A * | 11/1999 | Blewett | A61B 18/1477 600/105 |
| 6,071,280 | A | 6/2000 | Edwards et al. | |
| 6,106,521 | A * | 8/2000 | Blewett | A61B 18/1477 600/105 |
| 6,278,895 | B1 | 8/2001 | Bernard | |
| 6,428,538 | B1 * | 8/2002 | Blewett | A61B 18/1485 606/41 |
| 6,638,275 | B1 * | 10/2003 | McGaffigan | A61B 18/1477 606/41 |
| 8,251,991 | B2 | 8/2012 | Epstein et al. | |
| 2002/0061589 | A1 | 5/2002 | King et al. | |
| 2003/0114846 | A1 | 6/2003 | Fuimaono et al. | |
| 2006/0058597 | A1 | 3/2006 | MacHado et al. | |
| 2007/0016183 | A1 | 1/2007 | Lee et al. | |
| 2007/0038181 | A1 | 2/2007 | Melamud et al. | |
| 2009/0131855 | A1 | 5/2009 | Young et al. | |
| 2009/0254019 | A1 | 10/2009 | Gehl et al. | |
| 2010/0298761 | A1 | 11/2010 | Staal et al. | |
| 2011/0152858 | A1 | 6/2011 | Long et al. | |
| 2012/0271277 | A1 | 10/2012 | Fischell et al. | |
| 2012/0310236 | A1 | 12/2012 | Placek et al. | |
| 2013/0178910 | A1 * | 7/2013 | Azamian | A61B 17/00234 607/33 |
| 2013/0296995 | A1 | 11/2013 | Mahmood et al. | |
| 2014/0039586 | A1 | 2/2014 | Barker et al. | |

OTHER PUBLICATIONS

EP Extended European Search Report in European Appln. No. 15768062.0, dated Sep. 27, 2017, 9 pages.
PCT International Preliminary Report on Patentability in International Appln. No. PCT/US2015/022145, dated Sep. 27, 2016, 7 pages.
PCT International Search Report and Written Opinion in International Appln. No. PCT/US2015/022145, dated Jun. 24, 2015, 6 pages.

* cited by examiner

EXPANDABLE CATHETER DEVICES ELECTRODE ARRAY

CROSS REFERENCE TO RELATED APPLICATIONS

This application is a 371 National Stage Application of PCT/US2015/022145 filed on Mar. 24, 2015, which claims priority to and the benefit of U.S. Provisional Application No. 61/969,386, filed Mar. 24, 2014, and entitled, "Expandable Catheter Devices Electrode Array", the contents of both of which are herein incorporated by reference in their entirety.

FIELD OF THE INVENTION

The present invention relates to catheter devices electrodes, and more specifically to an expandable catheter devices electrode array.

BACKGROUND

In the treatment of diseases in the lung, e.g. lung cancer, as well as diseases in other anatomical areas of a body, physical access to a diseased or normal tissue region may be a challenge. This is especially the case if the diseased region lies deep within the body of the patient. Furthermore, efficient delivery and subsequent uptake of therapeutic molecules, such as a drug or genetic compound, to an anatomical target tissue is often a problem.

Electroporation is a known method used to deliver drugs and genetic material to various biologic tissues, where the uptake of these substances into tissue cells is enhanced through the application of electric pulses of specific amplitude. The delivery of drugs by electroporation is also known as electro-chemotherapy (ECT) and the delivery of genes as Gene Electro Transfer (GET). In ECT and GET applications, electroporation is used to create a transient permeabilization of the cell membranes in a target tissue area with the purpose of enhancing the uptake of the chemotherapeutic agents as well as the uptake and expression of genetic materials.

In addition to the delivery of therapeutic molecules, electroporation has a stand-alone application that is known as irreversible electroporation (IRE). In IRE, the amplitude of electric pulses is increased beyond the levels used in ECT and EGT, which creates a permanent permeabilization of the cell membranes in a target tissue area with the purpose of promoting cell death through cell leakage. A further application is the ablation of target tissue through the use of nanosecond pulse electric fields or the stimulation of cells through the application of nanosecond or picosecond pulse electric fields.

In order to provide an efficient application of pulse electric fields two or more electrode poles have to be brought into—or into close vicinity of—the region to be treated (target region). Examples of devices used for Electroporation are known from U.S. Pat. Nos. 5,674,267 and 6,278,895. These devices consist of an array of needle-type electrodes arranged as individual electrodes inserted via some external plate-shaped element providing a fixed distance between and relative position of the individual needles. If the target region is situated in a remote region of the body, such as the deeper regions of the lung or brain, the placement of electrodes may in itself be harmful to intervening tissue through which the electrodes need to traverse in order to be located in the desired region. Furthermore, a large access area must be available, and for applications in the brain this will entail creating a large hole in the patient's skull. Therefore, it is evident that the mentioned prior art devices are only well-suited for treatment in target regions in close proximity to an outer surface of the body, because an attempt to treat deeper-lying regions would cause excessive trauma to the intervening tissue.

There is thus a need for an electroporation device and an electroporation method that overcomes the shortcomings of the presently known devices and methods.

SUMMARY

Embodiments of the invention concern catheter devices and methods of using the same for the delivery of electrical treatments, alone or in combination with therapeutic agents. Catheter devices in accordance with the various embodiments can include an elongate housing extending along a major axis, the elongate housing comprising a first end with at least one opening. The catheter devices can also include an electrode assembly disposed in the elongate housing and including a plurality of deformable electrodes with respective electrode distal ends, where the electrode distal ends each consist of respective member portions and respective tip portions. In the catheter devices, the electrode assembly is slidably movable within the housing along the major axis to allow the electrode distal end portions to transition between a first position in which the electrode distal end portions are substantially enclosed in the elongate housing and a second position in which the electrode distal end portions extend from the at least one opening. Further, an average distance between the tip portions in the second position is configured to be greater than an average distance between the tip portions in the first position the tip portions are positioned substantially in a same plane when the electrode assembly is in the second position.

In the catheter devices, each of the tip portions can include respective elongate end portions, where the elongate end portions are non-parallel in the first position and substantially parallel in the second position. Further, the tip portions can be substantially rigid materials.

In the catheter devices, the member portions can consist of elastically deformable materials and the member portions are deformed elastically in the first position. Further, at least one of the elongate housing, the at least one opening, or the electrode assembly can be configured to elastically deform the member portions when the electrode distal ends are in the second position.

Alternatively, the member portions can be deformed elastically in the second position. In such configurations, the electrode assembly further can include at least one expansion element, where the at least one expansion element is configured to apply a force to elastically deform the member portions when the electrode distal ends are in the second position. The at least one expansion element can be at least one expansion spring. Further, the electrode assembly can include at least one substantially rigid structure, and wherein the at least one expansion element is mechanically coupled between the at least substantially rigid structure and the member portions. The rigid structure can be an additional electrode or a needle for delivering therapeutic agents.

In some configurations, the opening can include at least one lip portion and the electrode assembly can include at least one limit stopper, where the limit stopper and the lip portion are arranged so that the limit stopper contacts the lip portion when the electrode distal ends are in the second position to prevent further motion of the electrode assembly beyond the second position.

In some configurations, the catheter device can be integrated into other devices. For example, the catheter device can be integrated into a passage or channel of an endoscopy device.

It should be understood that the various embodiments are not limited to the arrangements and instrumentality shown in the drawings.

DETAILED DESCRIPTION

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

In view of the limitations of conventional methods and device, the various embodiments of the invention are directed to a novel electrode catheter devices consisting of a housing with an electrode assembly, where the electrode assembly including electrodes and/or needles that can retract and extend for providing both electrical treatment and administering therapeutic agents to internal tissues. Such internal tissues can include, but are not limited to, brain, heart, and lung tissues, as well as any other tissues or organs in which attempting to place a large array of electrodes and/or needles would result or necessitate traumatic injury of other tissues. In the various embodiments, the electrodes and needles, when extended, are arranged over a large area. In particular, the electrodes and needles in the catheter are configured to expand to cover an area larger than a cross-sectional area of the end of the catheter devices.

Figure 1:
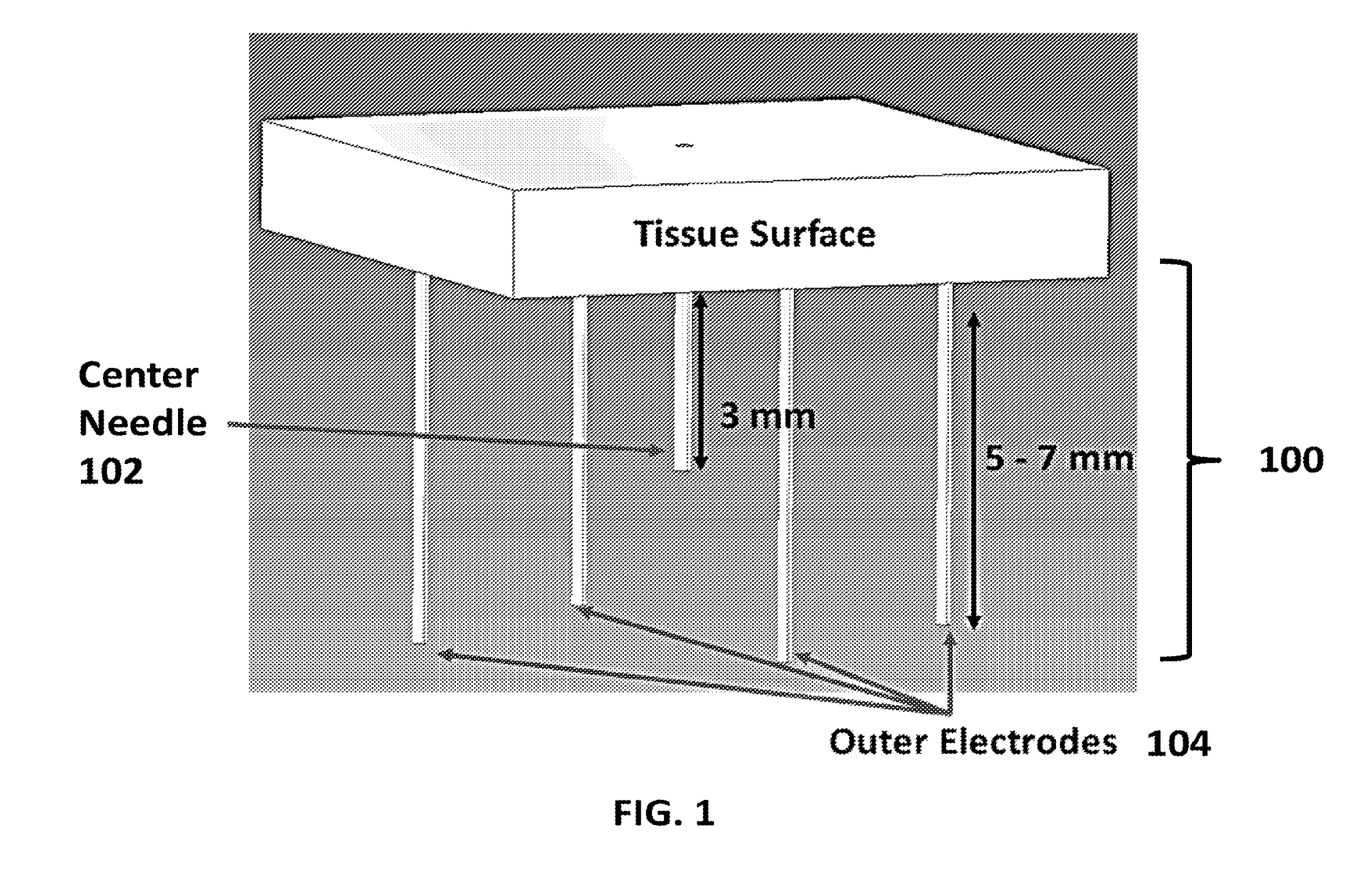
FIG. 1 shows an exemplary arrangement for an electrode assembly in accordance with the various embodiments of the invention.

In the various embodiments, the electrode assembly can be configured to support a variety of configurations for delivery of electrical treatments and administration of therapeutic agents. For example, the electrode assembly can be configured to consist of one or more needles for therapeutic agent delivery and a plurality of outer electrodes for delivering electrical treatments. An exemplary arrangement for such an electrode assembly 100 is shown in FIG. 1. As shown in FIG. 1, there can be a central needle 102 for delivery of therapeutic agents and four outer electrodes 104 for delivering electrical treatments. In some configurations, each electrode 104 can be configured to have an independent path to a source of electricity. This would allow each of the electrodes 104 to fire independently to form different electric field patterns across the electrodes 104.

Figure 2A:
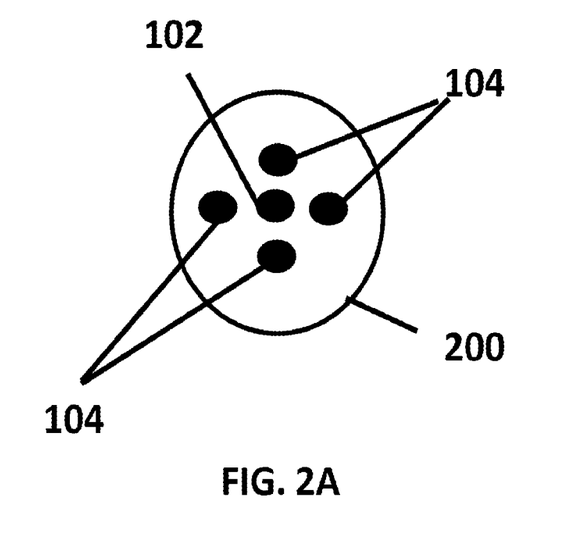
FIG. 2A schematically shows a catheter device including electrodes and needles that are retracted.

In the various embodiments, this arrangement of electrodes 104 and needle 102 would be sheathed inside an internal structure or housing (e.g., housing 408 of FIGS. 4A and 4B) of the catheter devices suitable for insertion into a blood vessel or other space in biological tissues until the specific location of the treatment is determined. This is illustrated in FIG. 2A, which schematically shows a catheter device 200 including electrode 104 and needles 102 that are retracted. In the various embodiments, such a catheter devices can be dimensioned such that the cross-section is between 1 and 10 mm, such as 3-5 mm. However, the various embodiments are not limited in this regard and other dimensions are suitable.

Figure 2B:
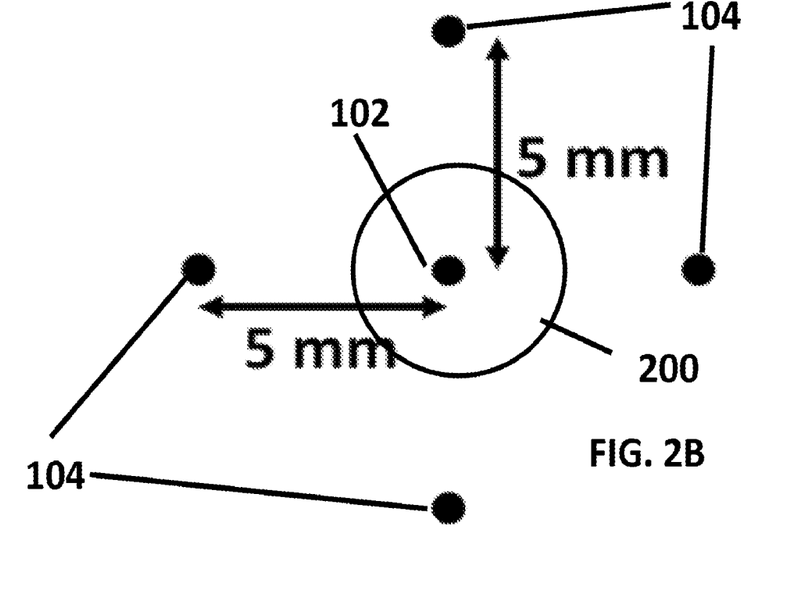
FIG. 2B schematically shows a catheter device including electrodes and needles that are extended.

In the various embodiments, once the end of catheter device 200 is positioned in an appropriate location, the electrode assembly (needle 102 and electrodes 104) is un-sheathed from the catheter devices and expands over a treatment area. This is illustrated schematically in FIG. 2B. FIG. 2B schematically shows catheter device 200 with electrodes 104 and needle 102 in the extended position. In one example, the electrodes 104 can extend so they are separated from needle 102 by 5 mm form a 5 mm×5 mm square treatment area.

Figure 3:
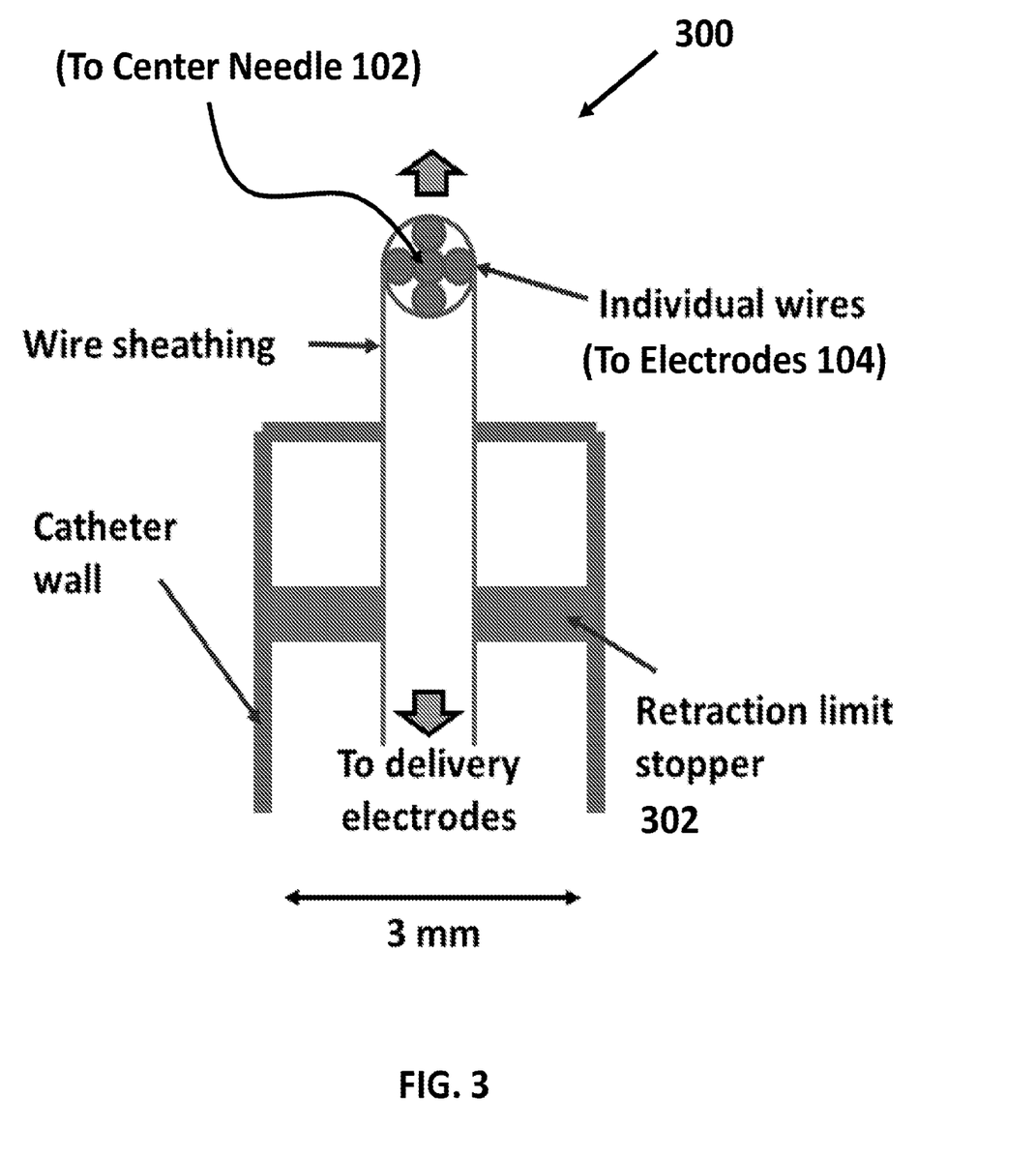
FIG. 3 shows a cross section of the distal tip of a catheter device in accordance with the various embodiments.

In one exemplary configuration, as shown in FIGS. 1, 2A, 2B, the electrode assembly 100 can be formed using five individual triple coated medical wires with >0.4 mm diameter. These can be bundled and fed through catheter device 200 to a distal tip of catheter device 200 with an opening. For example, an opening of ~3 mm diameter can be provided. First ends of the wires can be connected to a pulse delivery device (not shown) and second ends of the wires can be connected to retractable electrodes 104. A cross section of the distal tip 300 is depicted in FIG. 3. At least one retraction limit stopper or inner lip 302 can be designed into the catheter device 200 to provide a mechanism for the electrodes to be pulled too far in or out. These limits can be determined based on the desired configuration for the electrodes 104 when sheathed and/or unsheathed.

In operation, after the area of treatment is determined, the center needle 102 can be unsheathed to deliver the therapeutic agent. After the therapeutic agent is delivered, the center needle 102 can then be retracted and the 4 outer electrodes 104 are unsheathed to deliver the electrical pulse. The electrodes 104 can then be retracted prior to removing or repositioning the catheter device 200. However, the various embodiments are not limited to solely this arrangement. For example, in some configurations the center needle 102 can be unsheathed simultaneously with the electrodes 104. Moreover, the center needle 102 can also be configured to remain in an extended position while the electrodes 104 deliver electrical treatment. In some embodiments, the center needle 102 can also be configured to operate as an electrode. Additionally, depending on the desired shape for the treatment area, the electrodes can be arranged so that simultaneous extension or retraction is not required.

Each of the outer electrodes 104 can be electrically isolated to fire independently while being able to deliver high voltage (HV) pulses with voltages that can be 1 volt to 30 kV or even significantly higher and pulse length ranging from the millisecond to picoseconds range. In the various embodiments, the insulation material used for the catheter devices electrode can be selected to allow high degrees of flexibility while being able to withstand HV pulses (e.g., polymide insulated wires).

As noted above with respect to FIGS. 2A and 2B, the electrodes 104 are designed to expand once unsheathed from the catheter device 200. To provide this functionality, the electrodes 104 require some means to induce deformation and expand over the treatment area. Therefore, in some embodiments, the electrodes 104 can be constructed from shape-memory or spring loaded materials. Such materials can be configured to deform, when retracted, in order to conform to the internal structure of the catheter device 200. When extended or unsheathed, the memory properties or spring loaded properties of the materials can cause the extended parts of the electrodes 104 to deform and extend over a treatment area, as illustrated in FIG. 2A.

In the case of shape memory alloys (e.g., copper-aluminum-nickel or nickel-titanium), these can require heating or other stimulus to deform (or undeform). Thus, in such configurations, the catheter device 200 can include one or more heating elements or heating sources (not show) to cause such deformation/undeformation. For example, the deformed state for electrode 104 can be the sheathed state (i.e., conforming to the shape of the catheter device 200) and as the electrodes 104 are extended, heating can be applied to cause the electrodes 104 to return to their original shape in which the large treatment area is defined. It should be noted that the shape memory alloy incorporated into the electrodes need not be the current conducting portion of themselves. For example, a shape memory alloy can be attached to or embedded in the insulation for the electrodes.

In the case of spring loaded materials, the spring loaded materials can be configured such that when the electrodes 104 are extended or unsheathed, they can revert to a related state defining the treatment area. The deformed state for electrode 104 can then be the sheathed state in which the electrodes 104 are sheathed and conform to the shape of the catheter device 200. It should be noted that the spring loaded materials incorporated into the electrodes need not be the current conducting portion of themselves. For example, spring loaded materials can be attached to or embedded in the insulation for the electrodes.

In some configurations, the electrodes may also be prepared with/covered by/impregnated with a therapeutic agent that may be dissolvable in an electrical field. Thereby, the therapeutic agent can be released from the electrodes when an electrical field is applied to the target tissue via the electrodes. Thereby the need for needle 102 may be spared. However, the drug impregnated electrodes may also be used with embodiments with a needle 102 in order to release multiple agents simultaneously.

In some embodiments, in the unsheathed or extended position, the needle 102 and electrodes 104 can vertically extend the same height or a different height. For example, as shown in FIG. 1, the center needle 102 can have a penetration depth of 3 mm while the outer electrodes 104 can have a penetration depth of 5-7 mm. However, the various embodiments are not limited to the configuration in FIG. 1 and other arrangements and vertical heights can be provided for needles and electrodes.

A device in accordance with the various embodiments can therefore combine therapeutic agent delivery and electrical treatment for enhanced effects. The invention can be used in various capacities and fulfill many effects which can include but are not limited to:

(1) movement of molecules in the extra-cellular space;
(2) movement of molecules from the extra-cellular space through the barrier surrounding a living cell, such as the cell membrane, and into the cell;
(3) movement of molecules within the cell interior;
(4) movement of molecules from the cell interior through the barrier surrounding a living cell and into the extra-cellular space;
(5) a change in the properties of the barrier surrounding a living cell to make it more permeable to exogenous molecules;
(6) a change in the properties of a living cell to activate it or cause it to die;
(7) movement of molecules into the barrier surrounding a living cell;
(8) movement of molecules in a nonliving matrix;
(9) movement of cells in a medium;
(10) fusion of two or more cells; and
(11) movement of molecules through a tissue such as but not limited to skin blood vessels, endothelial linings, cardiac muscle, smooth muscle, and skeletal muscle.

As noted above, spring-loaded or shape memory alloy materials can be used in some embodiments to cause the electrodes 104 to expand to cover a larger area when extended or unsheathed. However, the various embodiments are not limited in this regard. In some embodiments, the electrodes 104 can be combined with expansion members (e.g., springs) to cause the necessary deformation. This is illustrated in FIGS. 4A and 4B.

Figure 4A:
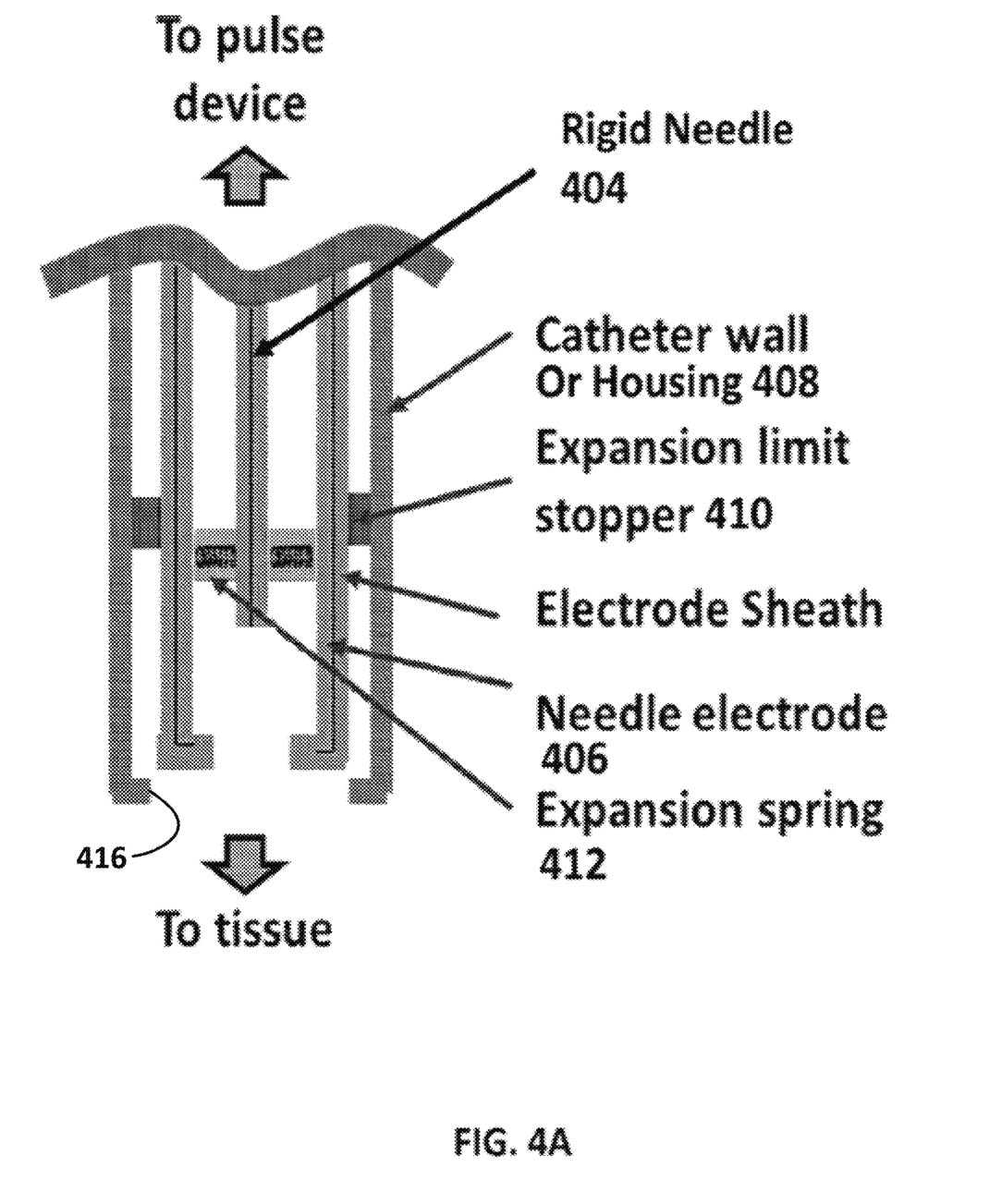
FIGS. 4A and 4B schematically illustrate an alternate configuration for catheter devices in sheathed and unsheathed configurations, respectively, in accordance with the various embodiments.
Figure 4B:
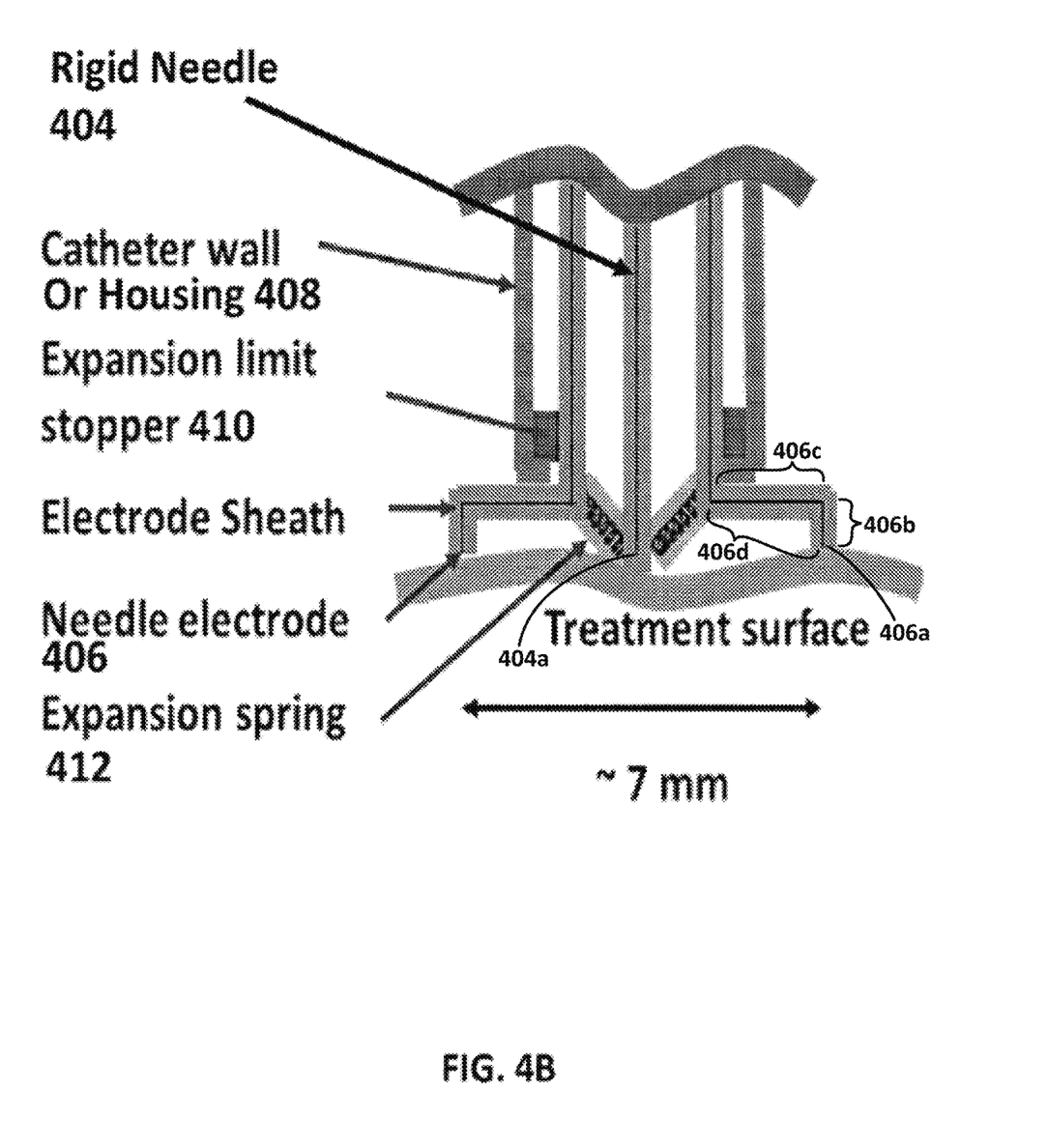

FIGS. 4A and 4B schematically illustrate an alternate configuration for catheter devices 400 in sheathed and unsheathed configurations, respectively, in accordance with the various embodiments. As with catheter device 200 discussed above, the catheter devices 400 can include an electrode assembly 402, consisting of one or more substantially rigid needles 404 and a plurality of flexible electrodes 406, a housing 408, and, optionally, one or more limit stoppers 410. In addition to the foregoing components, catheter devices 400 can further include expansion elements, such as expansion springs 412, mechanically attaching the rigid needles 402 to the flexible electrodes 408.

In the sheathed or retracted configuration of the electrode assembly 402, as shown in FIG. 4A, the flexible electrodes 406 and needles 404 are pulled within the housing 408 of catheter devices 400. As a result, the flexible electrodes 406 are forced to conform to the housing 408. Since the needles 404 are selected to be substantially rigid, the conforming of flexible electrodes 406 causes the expansion springs 412 to be compressed between the conforming flexible electrodes 406 and the substantially rigid needles 404. In configurations including limit stoppers 410, the housing can include at least one inner lip 302 (FIG. 3) that engages with the limit stoppers 410 to prevent the electrode assembly 402 from being retracted too far into the catheter devices 400.

In the unsheathed or extended configuration of the electrode assembly 402, as shown in FIG. 4B, the flexible electrodes 406 can be deformed so that a treatment area larger than a cross-sectional area of the catheter devices 400 is provided. Further, the flexible electrodes 406 can also be deformed so that that the tips 406a of the electrodes 406 and the tips 404a the needles 404 lie in substantially a same plane, as shown in FIG. 4B. In the configuration of FIG. 4B, the deformation of flexible electrodes 406 is caused by expansion springs 412. That is, since needles 404 are selected to be substantially rigid, any force stored in expansion springs 412 is applied to the flexible electrodes 406.

The flexible electrodes 406 can be configured such that when the expansion springs apply force to thereto, the tips 406a of the electrodes 406 not only lie in substantially the same plane, but tip portions 406b of the electrodes 406 also are substantially parallel to each other. As a result, of such a configuration, the electric fields generated by such electrodes 406 are more predictable and can be more accurately controlled. In one exemplary configuration, as illustrated in FIG. 4B, the flexible electrodes 406 are deformed by expansion springs 412 by approximately 90 degrees. Thus, the member portions 406c of the flexible electrodes 406 can be configured to extend perpendicular to the other portions of the flexible electrodes 406 such that when the flexible electrodes 406 are deformed by 90 degrees, the tip portions 406b and the tips 406a of the flexible electrodes 406 will be positioned correctly. However, the various embodiments are not limited in this regard and the arrangement and deformation of the flexible electrodes 406 and electrode distal ends 406d thereof can vary to accommodate different amounts of deformation by expansion springs 412.

In configurations including limit stoppers 410, the housing can include at least one outer lip 416 that engages with the limit stoppers 410 to prevent the electrode assembly 402 from being extended too far out of catheter devices 400. This also serves to ensure that the arrangement of the ends of the flexible electrodes 406 is correct when flexible electrodes 406 have been deformed by expansion springs 412.

In the configuration shown in FIGS. 4A and 4B, the electrode assembly is shown as being configured such that needles 404 and flexible electrodes 406 are deployed simultaneously. However, the various embodiments are not limited in this regard. In other configurations, the needles 404 and the flexible electrodes 406 can be configured so that they can be deployed in different groups or even individually.

Figure 5:
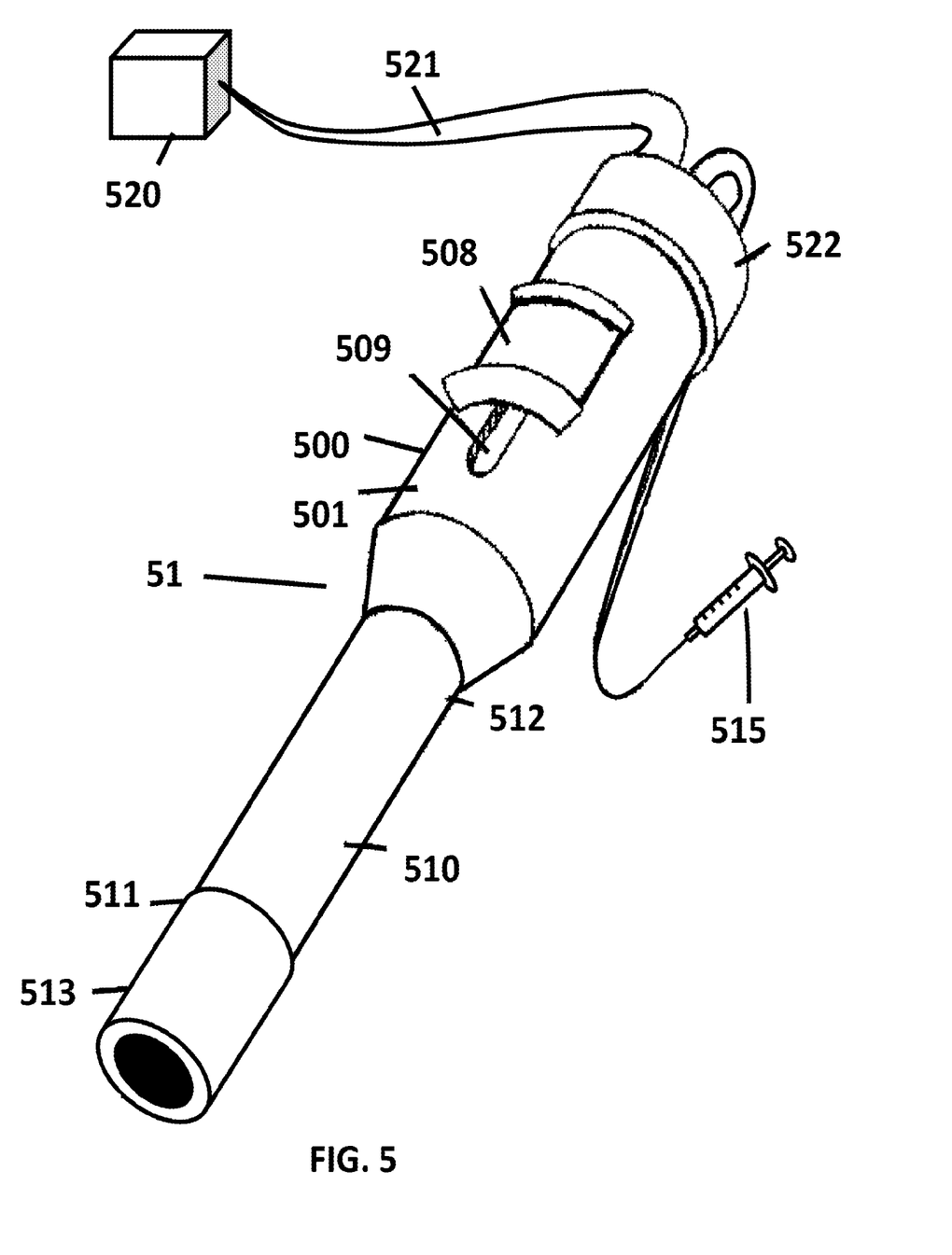
FIG. 5 shows an electrode introducing catheter device according to an embodiment of the invention.

In FIG. 5 an electrode introducing catheter device 51 according to an embodiment of the invention is shown. The catheter device 51 comprises a handle section 500 and an elongate introducer shaft 510 preferably having a length suitable for accessing deeper-lying tissue regions. In some embodiments, the handle section 500 can be configured as a generally cylindrical housing 501 that is preferably formed in plastic or another suitable material. The type and length of the shaft 510 may be adapted for the intended use. For example, based on the application, the shaft 510 can be rigid or flexible. The shaft 510 is attached to the handle section 500, and has a proximal end 512 adjacent to the handle section 500 and a distal end 511. The shaft may in one embodiment be fixedly attached to the handle section. In other embodiments the shaft may be detachably mounted to the handle section 500, and may comprise suitable means for establishing temporary connections, e.g. for conducting electrical pulses. A distal tip 513, that can be shaped to permit the creation of a channel through intervening layers of tissue while causing minimal damage to said tissue, is disposed at the distal end 511 of said shaft 510.

The handle section 500 can also include a deployment slider 508 that is movable between a first retracted and a second advanced position within and relative to the handle. The deployment slider 508 can have portions slidably held in grooves 509 in the handle. The distal tip 513 can be configured to provide electrodes and needles as described above with respect to FIGS. 1, 2A, 2B, 3, 4A, and 4B. In operation, the deployment slider 508 can cause the extension and retraction described above with respect to FIGS. 1, 2A, 2B, 3, 4A, and 4B. Although a single slider is illustrated in FIG. 5, in other embodiments multiple sliders can be provided to control the extension and retraction of needles and electrodes by group or individually, as discussed above.

The distal tip 513 can have, in some configurations, a rounded, non-cutting shape or any other shape. In other embodiments (not shown) the distal tip may be provided with a cutting edge or a pointed tip, i.e. a sharpened tip. These latter embodiments are e.g. well-suited for percutaneous applications. In either case, the distal tip 513 may be formed integrally with the introducer shaft 510 or it may be a formed as a separate part coupled to the distal end 511 of the introducer shaft 510. With a removable/detachable tip 513, and/or a detachable shaft 510, the length and thereby the reach of the device, may be adapted, by a suitable choice of shaft. Further, this allows for use of single-use only parts for the parts that are inserted into a patient. Thereby, the need for disinfection of the parts to be inserted into a patient may be eliminated.

The introducer shaft 510 can include a delivery channel (not shown) provided through the shaft 510 from the proximal end 512 to the distal end 511 along a longitudinal or major axis of said shaft 510, and terminating through said distal tip 513. The channel can have a proximal end and a distal end. The distal end of the channel can be coupled to one or more needles provided in the distal tip 13 in order to administer therapeutic agents. It should be noted that such a channel may split up into a multitude of minute channels at the distal end, each being associated with a different needle at the distal tip 513. The proximal end of the channel extends through the shaft 510 to the handle section 500, and is adapted for connection to a drug/genetic material delivery means (515) comprising a storage of a drug/medicament and/or means (e.g. a pump or a piston or the like) for advancing said medicament from said storage and through said channel to a target tissue. In a simple form the delivery means may be provided by a syringe 515, connected to the delivery channel via the handle section 500, e.g. by a tubing.

In an alternative embodiment (not shown), the channel may be configured to receive an elongate delivery system, e.g. in the form of a tubing, that may reach from the storage means into the region to be treated. Such a delivery system may comprise a syringe connected to said tubing, in such a way that the channel is adapted to receive e.g. a distal section of said tubing.

In yet another alternative embodiment (not shown), the catheter device 51 may provide an integrated therapeutic agent delivery system comprising delivery means with advancing/pumping means and/or a storage for a therapeutic agent, being integrated in the handle section 500.

The electroporation catheter device 51 and the delivery channel may also be configured by e.g. appropriate coupling means and/or dimensioning to receive and guide for instance an ultrasound probe, imaging device, a surgical tool or another tool for minimally invasive manipulation of tissue. Thus the device 1 can be used in a flexible way, where for example it is not necessary to remove the catheter device 51 and replace it with another specialized surgical tool, if the operator/surgeon encounters unexpected obstacles/difficulties prior to, during or following the electroporation process.

The shaft 510 can further include a plurality of guide channels (not shown) and extending from the proximal end 512 to the distal end 511 of the shaft 510, and through the distal tip 513. Each guide channel can be adapted for guiding one or more wires for the electrodes in the distal tip 513. These wires can be moved, as necessary, to effect the retracted and extend positions for the electrode assembly if the catheter device 51.

In an alternative embodiment (not shown) each guide channel may be provided, at least along a section of the shaft 510, by individual tubes in the shaft 510.

In use, the wires in the catheter devices are connected to a suitable electric stimulus generator 520 via connector 521 coupled to an end portion 522 of handle section 500. The catheter device 51 is then inserted in a subject. For example, through an orifice or an incision and is directed to the target region of the patient's body. Alternatively, the catheter can be guided through an existing orifice, airway, vessel, or other available path through the patient's body. The precise location may be identified by means of ultrasound, CT, MR or another suitable means, and the correct position of the introducer shaft 510 prior to deployment may be verified by similar means. As described above, in other embodiments, the stimulus generator may be integrated in the handle section.

When a correct position of the introducer shaft 510 has been obtained, an operator may deliver a suitable therapeutic agent into the tissue region to be treated. Delivery can be done by inserting the elongate, length-adjusted and properly dulled needle of a syringe 515 in the central hole of the end cap and advancing it until no further motion is possible. The operator may then empty the syringe 515 by pressing the syringe plunger, whereupon the liquid in the syringe is expelled into the tissue to be treated.

Before, during or upon delivery, the operator may deploy the electrodes in a predefined pattern, as previously described. Deployment is done by moving the deployment slider 508 from its first retracted position towards its second advanced position. This movement results in the motion of the electrodes from the first retracted position to the second extended position. Upon deployment, an operator may activate the electric stimulus generator 520 to deliver a sequence of preferably short and intense electric pulses, as discussed above, to the tissue to be treated. To ensure a suitable distribution of pulses and the consequent electric fields in the tissue to be treated (target tissue), pulses may be assigned to alternating specific electrodes in a pattern that may be tailored to suit the anatomy of the individual region of the body to be treated and/or the geometry of the specific target tissues.

Although the catheter devices of the various embodiments are described for delivering therapeutic agents and electric pulses contemporaneously, the various embodiments are not limited in this regard. That is, the catheter devices of the various embodiments can be used for delivering pulses without therapeutic agents.

Further, although the various embodiments have been primary directed to devices for use in the delivery of electrical treatments and/or therapeutic agents, the various embodiments are not limited in this regard. In some embodiments, the principles of operation described here can be also utilized to provide catheter devices with grasping tools on the end. For example, the electrodes shown in FIGS. 4A and 4B can be configured have sufficient rigidity so that during retraction of said electrodes, the electrodes are capable of grasping items. That is, as the electrodes shift from their extended position to a retracted position, the end can serve to grasp and secure an object. In such configurations, the end of the electrode can be configured to have an orientation that is conducive to the grasping of objects.

Figure 6A:
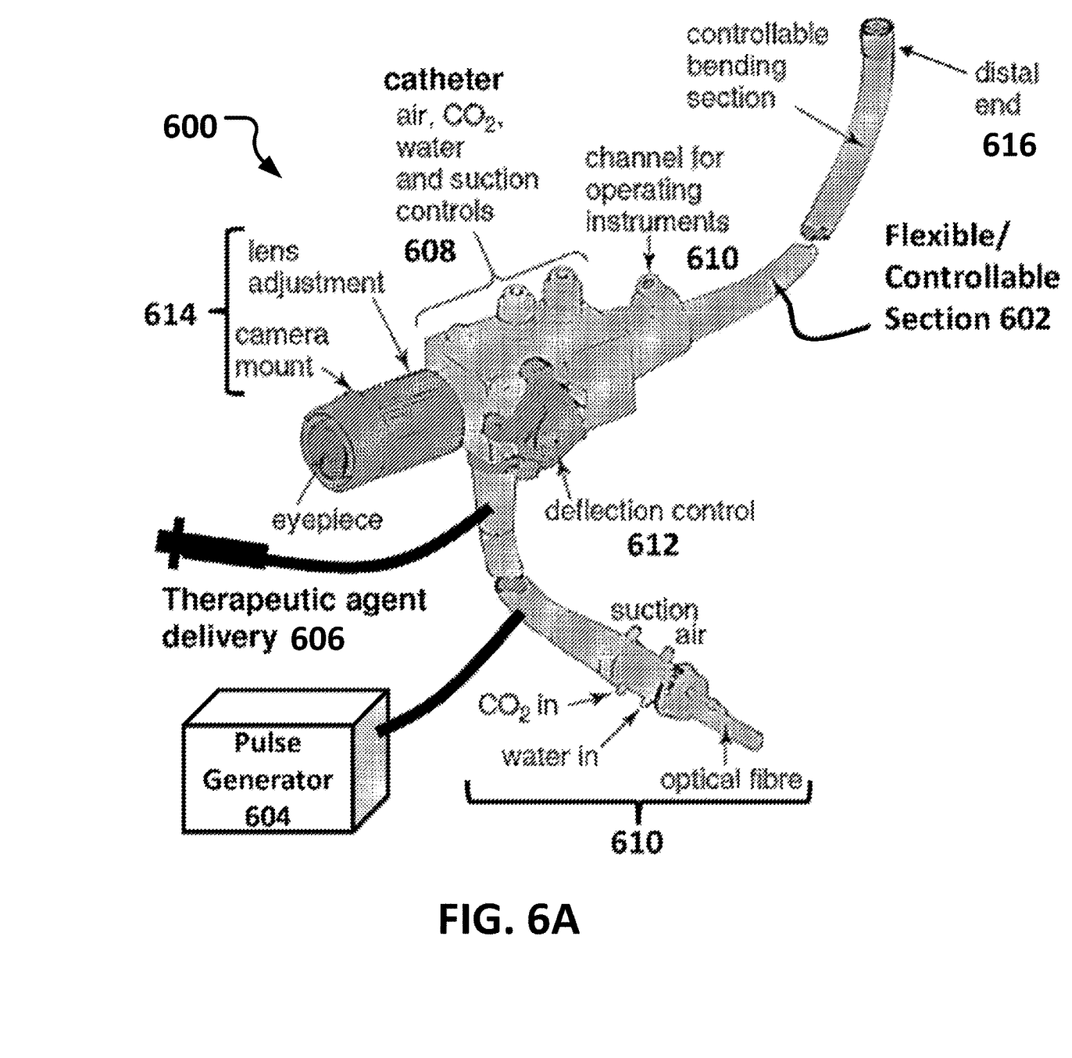
FIG. 6A shows a schematic of an endoscopy device configured in accordance with the various embodiments.
Figure 6B:
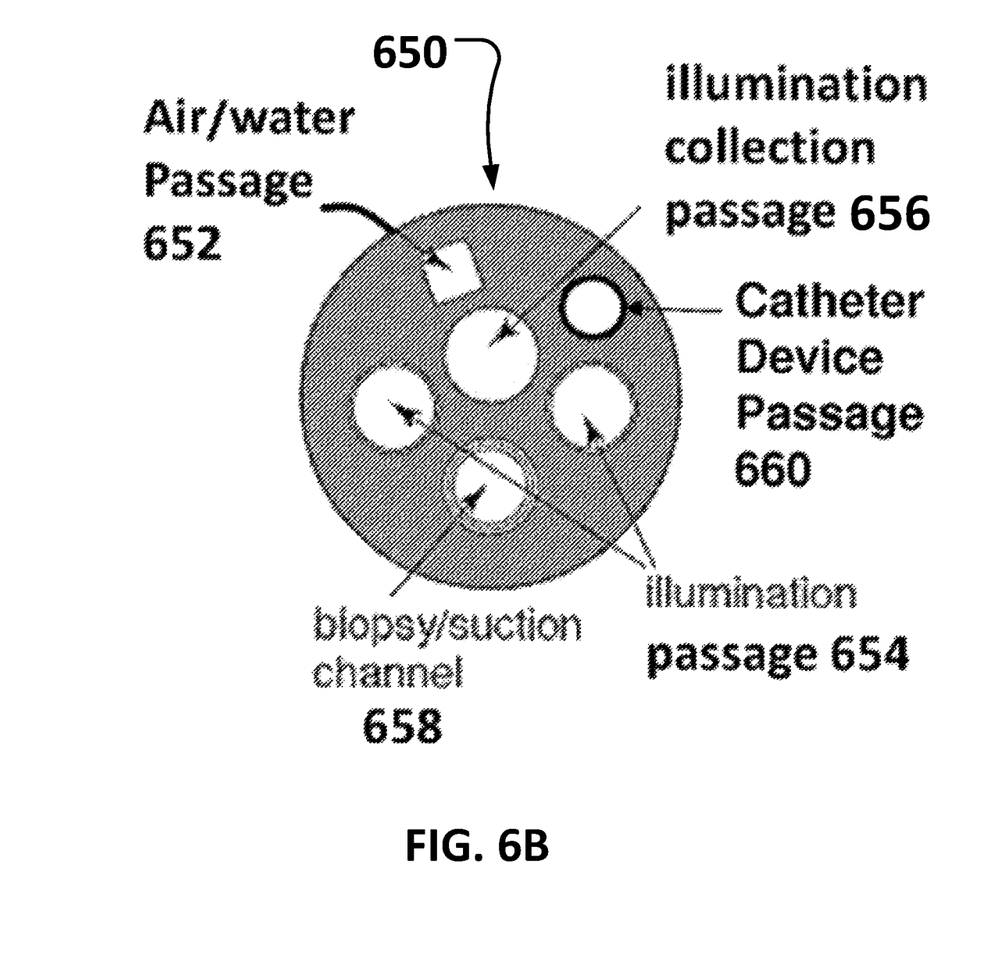
FIG. 6B shows a schematic of the cross-section of the flexible/controllable section of the endoscopy device of FIG. 6A.

It should be noted that while the catheter device described above is shown as a separate, standalone device, the various embodiments are not limited in this regard. That is, in some embodiments, the catheter device may be intergraded into other devices. For example, the catheter of the various embodiments can be integrated into an endoscope. As used herein, the term "endoscope" or "endoscopy device" refers to any device or instrument used to examine the interior of a body or other object. These include, but are not limited to, encephaloscopes, laryngoscopes, esophagoscope, thoracoscopes, angioscopes, nephroscopes, colonoscope, proctoscope, arthroscopes, rhinoscopes, esophagoscopes, bronchoscopes, mediastinoscopes, gastroscopes, laparoscopes, amnioscopes, cystoscopes, and hysteroscopes. One exemplary configuration is illustrated in FIGS. 6A and 6B. However, other configurations, with more or less components than shown are possible.

FIG. 6A shows a schematic of an endoscopy device 600 configured in accordance with the various embodiments, FIG. 6B shows a schematic 650 of the cross-section of the flexible/controllable section 602 of the endoscopy device 600.

As shown in FIG. 6A, the endoscopy device 600 can be configured many of the same components shown in FIG. 5, including, but not limited to generator 604 for generating electric pulses, a syringe 606 for providing therapeutic agents, and controls 608 for deploying the catheter device therein and controlling other components. The device 600 can also include other components for operating the device 600 in a conventional mode, such as components 610 for providing gases, liquids, suction, illumination, components 612 for control of the flexible/controllable section 602, and visualization components 614.

Further, as shown in FIG. 6B, in addition to the typical passages or channels for an endoscope (air/water 652, illumination 654, illumination collection 656, and biopsy/suction 658), an endoscope in accordance with the various embodiments can also include a catheter device channel or passage 660. Thus, the components of the catheter device can be disposed in passage 660, instead of a separate housing, and operate in substantially the same manner as such components in FIG. 5. In operation, the electrodes would slidably move within passage 660 and extend out of the distal end 616 of the flexible/controllable section 602 of the endoscopy device 600.

Additionally, while the various embodiments been described primarily with respect to medical or surgical application, the various embodiments are not limited in this regard. For example, the catheters of the various embodiments can also be used for treatment and/or repair of mechanical systems. In such cases, the catheter devices can be used for grasping objects, delivering agents that need to be activated by electrical pulses, or to deliver electrical pulses or perform electrical measurements in normally inaccessible region. Other non-medical or non-surgical uses are also possible.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising." Additionally, the term "substantially" or variants thereof are used in either the detailed description and/or the claims, such a term is intended to refer to being within 20% of the stated value or property.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A catheter device, comprising:
   an elongate housing extending along a major axis, the elongate housing comprising a first end with at least one opening; and
   an electrode assembly disposed in the elongate housing and comprising a plurality of deformable electrodes with respective electrode distal ends and respective electrode tips, the electrode distal ends each comprising respective member portions and respective tip portions,
   wherein the electrode assembly is slidably movable within the housing along the major axis to allow the electrode distal ends to transition between: (i) a first position in which the electrode distal ends are substantially enclosed in the elongate housing and the respective tip portions angularly extend radially inward from the respective member portions, and (ii) a second position in which the electrode distal ends extend from the at least one opening and the respective tip portions angularly extend from the respective member portions, and
   wherein an average distance between the tip portions in the second position is greater than an average distance between the tip portions in the first position, and
   wherein: (i) the electrode tips are positioned substantially in a same plane and (ii) the tip portions extend distally and substantially parallel to each other when the electrode assembly is in the second position.

2. The device of claim 1, wherein the member portions comprise elastically deformable materials.

3. The device of claim 2, wherein member portions are configured to be deformable elastically in the second position.

4. The device of claim 3, wherein the electrode assembly further comprises at least one expansion element, the at least one expansion element is configured to apply a force to elastically deform the plurality of deformable electrodes when the electrode distal ends are in the second position.

5. The device of claim 4, wherein the at least one expansion element comprises at least one expansion spring.

6. The device of claim 3, wherein the electrode assembly further comprises at least one substantially rigid electrode, and wherein the at least one expansion element is mechanically coupled between the at least one substantially rigid electrode and the member portions.

7. The device of claim 4, wherein the at least one expansion element is configured to deform the plurality of deformable electrodes such that the tip portions extend approximately perpendicular to the member portions.

8. The device of claim 2, wherein the member portions comprise shape-memory or spring-loaded material.

9. The device of claim 1, wherein the respective tip portions extend from the respective member portions at an angle in the first position that is equal to the angle at which the respective tip portions extend from the respective member portions in the second position.

10. The device of claim 9, wherein the angle at which the respective tip portions extend from the respective member portions in the first and second positions is substantially 90 degrees.

11. The device of claim 1, further comprising:
    at least one needle extending coaxially along said major axis and configured for delivering an agent; and
    at least one expansion element mechanically attaching the at least one needle to the plurality of deformable electrodes.

12. The device of claim 1, wherein the at least one opening comprises at least one lip portion, wherein the electrode assembly further comprises at least one limit stopper, and wherein the at least one limit stopper and the at least one lip portion are arranged so that the at least one limit stopper contacts the at least one lip portion when the electrode distal ends are in the second position to prevent further motion of the electrode assembly beyond the second position.

13. The device of claim 1, further comprising at least one expansion element configured to deform the plurality of deformable electrodes to provide a treatment area larger than a cross-section area of the device.

14. The device of claim 1, wherein the tip portions comprise substantially rigid materials.

15. The device of claim 1, further comprising at least one needle extending coaxially along said major axis and configured for delivering an agent.

16. The device of claim 1, wherein the electrode assembly is configured to deliver pulses with pulse length ranging from milliseconds to picoseconds.

17. The device of claim 1, further comprising one or more deployment sliders configured to control extension and retraction of the electrode assembly, or wherein the one or more deployment sliders are configured to control extension and retraction of an individual or a group of electrodes of the electrode assembly.

18. The device of claim 1, wherein the device further comprises a grasping tool.

19. The device of claim 1, wherein at least one of the plurality of deformable electrodes is configured for delivering an agent or suction.

20. The device of claim 1, wherein at least some deformable electrodes of the plurality of deformable electrodes are configured to be fired independently from other deformable electrodes of the plurality of deformable electrodes.

21. The device of claim 1, wherein at least some deformable electrodes of the plurality of deformable electrodes are coated with a therapeutic agent that is dissolvable in an electric field.

22. A catheter device, comprising:
an elongate housing defining a major axis and a distal end opening; and
a plurality of electrodes disposed in the elongate housing, each electrode comprising a proximal end and a distal end, each distal end comprising:
a member portion attached to a respective proximal end, and
a tip portion attached to a respective member portion, each tip portion terminating at an electrode tip,
wherein each electrode is movable between:
a first position in which: (i) the distal end of the electrode is in the elongate housing, (ii) the member portion of the electrode is collinear with its respective proximal end, and (iii) the tip portion of the electrode extends at a non-zero angle from its respective member portion, and
a second position in which: (i) the distal end of the electrode extends from the distal end opening, (ii) the member portion of the electrode is noncollinear with its respective proximal end, and (iii) the tip portion of the electrode extends at the non-zero angle from its respective member portion,
wherein the tip portions of any of the plurality of electrodes, when in the second position, are substantially parallel to each other.

23. The device of claim 22, further comprising at least one expansion element configured to deform the plurality of electrodes, while the plurality of electrodes is in the second position, to provide a treatment area larger than a cross-section area of the device.

24. The device of claim 23, wherein the at least one expansion element is configured to deform the plurality of electrodes such that the tip portions extend approximately perpendicular to the member portions.

25. The device of claim 22, wherein the device is configured to deliver pulses, from the plurality of electrodes, with pulse lengths ranging from milliseconds to picoseconds.

26. The device of claim 22, further comprising one or more deployment sliders configured to control extension and retraction of an individual or a group of electrodes of the plurality of electrodes.

* * * * *

UNITED STATES PATENT AND TRADEMARK OFFICE
CERTIFICATE OF CORRECTION

PATENT NO. : 10,668,278 B2  
APPLICATION NO. : 15/311130  
DATED : June 2, 2020  
INVENTOR(S) : Richard Heller et al.

Page 1 of 1

It is certified that error appears in the above-identified patent and that said Letters Patent is hereby corrected as shown below:

In the Specification

In Column 1, Line 15, before the "FIELD OF THE INVENTION", please insert the following:
-- STATEMENT REGARDING FEDERALLY SPONSORED RESEARCH OR DEVELOPMENT
This invention was made with government support under NIH HL089017 awarded by The National Institute of Health. The government has certain rights in the invention. --

Signed and Sealed this
Fourteenth Day of December, 2021

Drew Hirshfeld
*Performing the Functions and Duties of the
Under Secretary of Commerce for Intellectual Property and
Director of the United States Patent and Trademark Office*